(12) United States Patent
Shipp, Jr.

(10) Patent No.: US 6,787,490 B2
(45) Date of Patent: Sep. 7, 2004

(54) GLOVE DONNING DELIVERY SYSTEM

(75) Inventor: Peter W. Shipp, Jr., Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 181 days.

(21) Appl. No.: 10/027,202

(22) Filed: Dec. 26, 2001

(65) Prior Publication Data

US 2003/0119399 A1 Jun. 26, 2003

(51) Int. Cl.⁷ ............................................. B32B 27/04
(52) U.S. Cl. ...................... 442/123; 424/400; 424/401; 424/402; 424/404; 424/405; 424/407; 424/414; 442/50; 442/54; 442/58; 442/79; 442/124; 442/125; 442/374
(58) Field of Search ........................... 442/50, 54, 58, 442/79, 123, 124, 125, 374; 424/400, 401, 402, 404, 405, 407, 414, 444, 445

(56) References Cited

U.S. PATENT DOCUMENTS

| | | |
|---|---|---|
| 3,411,982 A | 11/1968 | Kavalir et al. |
| 3,650,882 A | 3/1972 | Thomas |
| 3,813,695 A | 6/1974 | Podell, Jr. et al. |
| 3,967,623 A | 7/1976 | Butterworth et al. |
| 4,001,472 A | 1/1977 | Thomas et al. |
| 4,003,509 A | 1/1977 | Camarero |
| 4,075,382 A | 2/1978 | Chapman et al. |
| 4,100,324 A | 7/1978 | Anderson et al. |
| 4,166,001 A | 8/1979 | Dunning et al. |
| 4,310,928 A | 1/1982 | Joung |
| 4,548,844 A | 10/1985 | Podell et al. |
| 4,575,476 A | 3/1986 | Podell et al. |
| 4,589,873 A | 5/1986 | Schwartz et al. |
| 5,048,589 A | 9/1991 | Cook et al. |
| 5,284,703 A | 2/1994 | Everhart et al. |
| 5,322,918 A | 6/1994 | Kirby |
| 5,399,412 A | 3/1995 | Sudall et al. |
| 5,417,968 A | 5/1995 | Staats |
| 5,494,554 A | 2/1996 | Edwards et al. |
| 5,595,807 A | 1/1997 | Gooding, Jr. et al. |
| 5,767,163 A | 6/1998 | Kundsin |
| 5,776,306 A | 7/1998 | Hepford |
| 5,869,072 A | 2/1999 | Berry |
| 5,885,697 A | 3/1999 | Krzysik et al. |
| 5,919,471 A | 7/1999 | Saferstein et al. |
| 5,993,923 A | 11/1999 | Lee |
| 6,077,590 A | 6/2000 | Archer et al. |
| 6,228,385 B1 | 5/2001 | Shick |
| 6,273,996 B1 | 8/2001 | Hollenberg et al. |

FOREIGN PATENT DOCUMENTS

| | | |
|---|---|---|
| EP | 0 032 793 | 7/1981 |
| EP | 0 869 216 | 10/1998 |
| WO | 95/00097 | 1/1995 |
| WO | 97/29742 | 8/1997 |
| WO | 00/59450 | 10/2000 |
| WO | 01/00156 | 1/2001 |
| WO | 01/00253 | 1/2001 |
| WO | 01/08541 | 2/2001 |
| WO | 01/47699 | 7/2001 |

OTHER PUBLICATIONS

National Guideline Clearinghouse, APIC Guideline for handwashing and hand antisepsis in health care settings, Dec. 11, 2001, 1–5.

Alicia J. Mangram, MD; Teresa C. Horan, MPH, CIC; Michele L. Pearson, MC; Leah Christine Silver, BS; William R. Javis, MD; Guideline for Prevention of Surgical Site Infection, 1999, 247–278.

Division of Healthcare Quality Promotion (DHQP), Issues in Child Care Settings, 1/97, 1–3.

Division of Healthcare Quality Promotion, Issues in Healthcare Settings, 1985, 1–28.

Primary Examiner—Arti R. Singh
(74) Attorney, Agent, or Firm—Steven D. Flack; Dana E. Stano; Vincent T. Kung

(57) ABSTRACT

A substrate includes a flexible substantially planar sheet of at least one layer. The layer has a front side and a back side with a donning agent associated with at least one side of the sheet. The donning agent is transferable from the sheet to an object or individual apart from the sheet.

19 Claims, 1 Drawing Sheet

GLOVE DONNING DELIVERY SYSTEM

FIELD OF THE INVENTION

The present invention relates to glove donning. In particular, the present invention relates to towels used by surgeons or other medical practitioners after scrubbing, and prior to gowning/dressing up, and their methods of use.

BACKGROUND OF THE INVENTION

Medical personnel such as doctors, nurses, paramedics and the like, frequently use natural rubber gloves to protect their patients and themselves from potential bacteriological or viral contamination during medical procedures. Prior to the donning of such gloves, medical personnel disinfect their hands by thoroughly scrubbing and rinsing them under hot water, and in some circumstances, with antiseptic/antimicrobial agents, as part of hand/forearm antisepsis. Towels are used to dry the hands after washing, but the hands remain somewhat damp, even though the towel has removed most of the water.

Donning of rubber gloves can be difficult even when the hands are dry. However, dampness of the hands increases the coefficient of friction between the gloves and the hands, making donning even more difficult. To aid in the donning of disposable gloves, donning agents (i.e., powders) are commonly used so that the gloves will go on to a hand easily without tearing, or causing much inconvenience. Such donning agents are usually incorporated on the inside surfaces of the disposable gloves, that is, the surface of the glove in contact with the user's skin. Alternatively, such donning agents are directly applied to the hands of the medical personnel just prior to glove donning. The direct application of such donning agents to the hands adds an additional and inconvenient step to the donning routine before a medical procedure. More importantly, such powders used in disposable gloves can be irritating and tend to dry the skin. In some instances, such powder (as in the case of starches) can lead to infections or allergic reactions (such as granuloma and problems with airisilization of protein) for the wearer of such gloves, or the recipient of the medical care, if such powder finds its way into an open wound.

Due to the hazards associated with powder, powder free glove technology has been developed. Generally, there have been two main powder-free solutions for disposable gloves. The first is a halogenation treatment, such as chlorination of natural rubber or other polymeric gloves. Such a step helps reduce the coefficient of friction of the gloves on the skin. However, chlorination also reduces tackiness of the outer surfaces of the glove, which decreases some of the tactile functionality that medical personnel desire in a glove. Such a treatment can also reduce the shelf-life of the gloves. Furthermore, chlorination of the gloves adds an additional, often nonuniform, and potentially hazardous step to the glove manufacturing process.

The second powder-free solution is the addition of a layer of synthetic polymers to the inner surfaces of the gloves during manufacture. Such synthetic polymers often include polyurethanes or other hydrophilic lubricious materials, such as silicone and surfactants. Such a treatment is an additional step in the manufacture of gloves, and application of an acceptable uniformity of such chemical treatments is an ongoing issue.

Therefore, there is a need for a method of donning gloves that can be conveniently, efficiently and effectively used by a wearer of rubber gloves, that will aid in the donning of such gloves after the hands are washed, and which avoids the sometimes nonuniform addition of substances to gloves during the glove manufacturing process. There is also a need for an article/delivery system which assists in the donning of gloves and which overcomes the issues previously described.

SUMMARY OF THE INVENTION

A substrate includes a flexible substantially planar sheet of at least one layer. The layer has a front side and a back side with a donning agent associated with at least one side of the sheet. The donning agent is transferable from the sheet to an object or individual apart from the sheet.

As an alternative, the donning agent is either a wetting agent, a substance that acts as a wetting agent, or a silicone. In one embodiment, such substrate is made from a nonwoven reinforced material.

In an alternative embodiment, the previously donned gloves are contacted with the substrate to facilitate donning of a second set of gloves over the first set of gloves.

DEFINITIONS

Figure 1:
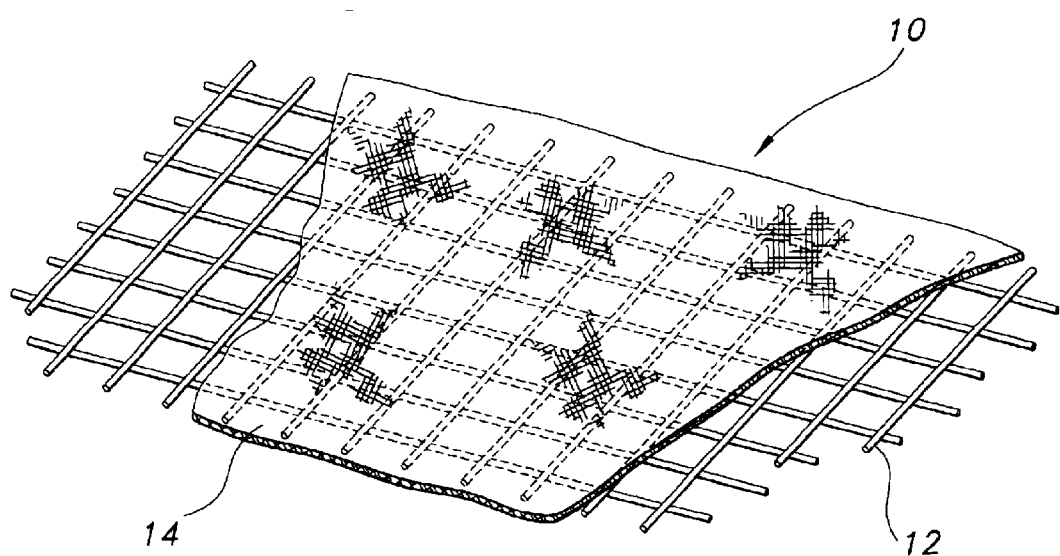
FIG. 1 is a fragmentary perspective view of one embodiment of a material constructed in accordance with the present invention.

As used herein, the term "comprising" is meant to be inclusive and open-ended, and does not exclude additional unrecited elements, compositional components, or method steps.

As used herein, the term "substrate" refers to a base material to which chemical treatments are applied either topically or throughout the body of, such as in the interstitial spaces, as by impregnation. The term "substrate" includes composite materials and materials having one or more layers.

As used herein, the term "substantially planar sheet" refers to an article that is primarily situated in the X-Y plane where the dimensions along the X-axis and Y-axis are much greater than the average dimension in the Z-axis. Although the article's surface may have surface characteristics such as ridges, undulations, texture, or the like, the dimension in the Z-axis is much less than the dimensions of the article in the X-Y plane. Such term refers to a substrate material that can be a woven fabric or knitted fabric such as a cellulosic fabric or cloth, or in the alternative a synthetic polymeric woven material that has been treated to be hydrophilic or is inherently hydrophilic and absorbent, a nonwoven cellulosic-based hydrophilic and absorbent web such as paper, or a nonwoven synthetic web that has been treated to be hydrophilic and absorbent, or a combination thereof. The term shall also include multiple layered sheet structures.

As used herein, the term "sterilizable" refers to the capability of the substrate or chemical treatment to be rendered free from reproductive spores or biological contaminants through known medical sterilization techniques, such as via exposure to ethylene oxide or ionizing radiation, such as gamma irradiation.

As used herein, the terms "lubricating agent" and "lubricant" shall be used interchangeably and shall refer to a material that is capable of reducing friction between two surfaces.

As used herein, the term "absorbent" refers to a material or substrate capable of absorbing moisture.

As used herein, the term "substance" includes one or more substances.

As used herein, the term "skin health agents" refers to substances that either promote the health of the skin, protects the skin, provides some other benefits to the skin such as a moisturizer, or a combination thereof. Numerous medicaments are known that are capable of providing therapeutic or health benefits to the skin. Such may result in softening, soothing, coating, pH balancing, lubricating, and/or cleaning the skin. Such materials include, but are not limited to astringents, antiseptic agents, antioxidants, antifungal agents, deodorants, enzyme inhibitors, emollients and so forth.

As used herein, the term "transferable" refers to the ability of a chemical treatment contained on or in a substrate, to be transferred, passed, or delivered from the substrate to a second location off of the substrate (such as onto the surface of another object or individual), by the action of contacting the substrate surface with the surface of another object/article or individual.

As used herein, the term "antimicrobial" refers to the ability to inhibit or control the spread or growth of microbes. An antimicrobial agent may be transferable from one object to another or in some way bound to an initial object.

As used herein, the term "residual" refers to material that remains on a substrate, even after some of it is transferred off of the substrate.

As used herein, the term "biocompatible" refers to a material that is compatible with living tissue.

As used herein, the terms "donning" or "to don" refers to the action of placing a glove on a hand or over another glove, that has previously been placed on a hand.

As used herein, the term "donning agent" refers to a substance that assists in donning.

As used herein, the term "towel" refers to a cloth, paper-based, or nonwoven material for wiping or drying things, or for drying oneself after washing or bathing.

As used herein, the terms "elastic" and "elastomeric" when referring to a fiber, film, fabric or cloth, mean a material which upon application of a biasing force, is stretchable to a stretched, biased length which is at least about 150 percent, or one and a half times, its relaxed, unstretched length, and which will recover at least 50 percent of its elongation upon release of the stretching, biasing force.

As used herein, the term "disposable" shall refer to an article, which is meant for one use, or limited use, and then is to be discarded.

As used herein, the term "cloth" shall refer to textile fabrics and felts. It includes any pliant fabric that is woven, knit, felted, needled, sewn, or similarly formed.

As used herein, the term "paper" shall refer to a sheet of plant fibers laid down on a fine screen from a water suspension, such as are is made via methods well known to those of ordinary skill in the art.

As used herein, the terms "nonwoven", "nonwoven fabric" and "nonwoven web" shall be used interchangeably and shall mean a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laying, carded web processes, and so forth.

As used herein, the term "meltblown fibers" means fibers formed by extruding a molten thermoplastic material through a plurality of fine die capillaries as molten threads or filaments into a high velocity gas (e.g. air) stream which attenuates the filaments of molten thermoplastic material to reduce their diameter, which can be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, which is incorporated herein by reference in its entirety.

As used herein, the term "spunbond fibers" refers to small diameter fibers which are formed by extruding a molten thermoplastic material as filaments from a plurality of fine capillaries of a spinnerette with the diameter of the extruded filaments then being rapidly reduced as by, for example, eductive drawing or other well-known spun-bonding mechanisms. The production of spun-bonded non-woven webs is illustrated in patents such as, for example, in U.S. Pat. No. 4,340,563 to Appel et al., and U.S. Pat. No. 3,692,618 to Dorschner et al, and U.S. Pat. No. 5,382,400 to Pike et al., which are incorporated herein by reference in their entirety.

As used herein, the term "coform" means a non-woven composite material of airformed matrix material comprising thermoplastic polymeric meltblown fibers such as, for example, microfibers having an average fiber diameter of less than about 10 microns, and a multiplicity of individualized absorbent fibers such as, for example, wood pulp fibers disposed throughout the matrix of polymer microfibers and engaging at least some of the microfibers to space the microfibers apart from each other. The absorbent fibers are interconnected by and held captive within the matrix of microfibers by mechanical entanglement of the microfibers with the absorbent fibers, the mechanical entanglement and interconnection of the microfibers and absorbent fibers alone forming a coherent integrated fibrous structure. These materials are prepared according to the descriptions in U.S. Pat. No. 4,100,324 to Anderson et al. U.S. Pat. No. 5,508,102 to Georger et al. and U.S. Pat. No. 5,385,775 to Wright, which are incorporated by reference herein in their entirety.

As used herein, the term "microfibers" means small diameter fibers having an average diameter not greater than about 100 microns, for example, having an average diameter of from about 0.5 microns to about 50 microns, or more particularly, microfibers may have an average diameter of from about 4 microns to about 40 microns.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries. In addition, it is to be further understood that reference to a polymer of any particular monomeric unit encompasses the presence of one or more additional components, in addition to the named monomer.

As used herein, the terms "stretch-bonded laminate" or "composite elastic material" refers to a fabric material having at least one layer of non-woven web, film or continuous filament array, with at least one of the layers of non-woven web, film or continuous filament array being elastic and at least one layer of the non-woven web (including pulp-based webs) being non-elastic, e.g., a gatherable layer. The elastic non-woven web layer(s), films, or arrays are joined or bonded in at least two locations to the non-elastic non-woven web layer(s). Preferably, the bonding is at intermittent bonding points or areas, while the non-woven web layer(s) are in juxtaposed configuration, and while the elastic non-woven web layer(s) (or fiber arrays) have a tensioning force applied thereto in order to bring the elastic non-woven web, or fiber array to a stretched condition. Upon removal of the tensioning force after joining of the web layers, an elastic non-woven web layer, film, or fiber array, will attempt to recover to its unstretched condition and will thereby gather the non-elastic non-woven web layer between the points or areas of joining of the two layers. The composite material is elastic in the direction of stretching of the elastic layer during joining of the layers and can be stretched until the gathers of the non-elastic non-woven web or film layer have been removed. A stretch-bonded laminate may include more than two layers. For example, the elastic non-woven web, film or fiber array, may have a non-elastic non-woven web layer joined to both of its sides while it is in a stretched condition so that a three layer non-woven web composite is formed having the structure of gathered non-elastic (non-woven web or film)/elastic (non-woven web, array or film)/gathered non-elastic (non-woven web or film). Yet other combinations of elastic and non-elastic layers can also be utilized. Such composite elastic materials are disclosed, for example, by U.S. Pat. No. 4,720,415 to Vander Wielen et al., and U.S. Pat. No. 5,385,775 to Wright, which are incorporated by reference herein in their entirety.

The gatherable layer can be a non-woven web of fibers, such as, for example, spunbonded webs, meltblown webs, air laid layer webs, bonded carded webs, hydroentangled webs, wet-formed (wet laid) webs such as cellulosic-based webs or any combination thereof. The gatherable layer may also be a mixture of fibers and one or more other materials such as, for example, wood pulp, staple-length fibers, particulates and super-absorbent materials. Such mixtures can be formed by adding fibers and/or particulates to the gas stream in which the meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials, such as disclosed in U.S. Pat. No. 4,100,324, to Anderson et al. which is incorporated by reference herein in its entirety.

The elastic layer can be an elastic film, an elastic web, elastic fibers or any combination thereof such as, for example, an elastic web containing elastic fibers/filaments. The elastic webs can also contain at least one layer of elastomeric meltblown fibers and optionally at least one layer of substantially parallel rows of elastomeric fibers/filaments in an array.

DETAILED DESCRIPTION

A glove donning delivery system that can be conveniently, efficiently and effectively used by a wearer of rubber gloves to aid in the donning of such gloves after the hands are washed, includes a hand towel that has been treated with a donning agent so that such donning agent is transferable from the hand towel to a user's hands during a hand drying process. In this fashion, the user of the hand towel can accomplish both the drying function while simultaneously treating the hands with a substance to facilitate the donning of elastomeric gloves. For the purposes of this application, the term "elastomeric" shall encompass natural latex rubber and synthetic rubber (nitrile) as well as other polymeric materials, which are elastic.

The disposable hand towel, which is specifically used during hand antisepsis, is desirably manufactured of a disposable flexible hydrophilic/absorbent cellulosic material substrate, such as a paper or tissue-based substrate. The substrate is a substantially planar sheet of at least one layer. The layer has a front or top side surface and a back or bottom side surface, and a donning agent associated with at least one side surface of the sheet. Furthermore, the donning agent may be associated with both sides of the sheet or impregnated throughout the sheet. The donning agent may only be associated with one side of a sheet in order to allow for greater absorbency on the other side of the sheet. The sheet, in alternative embodiments, may also include multiple layers, with the donning agent associated with less than all of the layers, to allow for higher absorbency on one layer than another. The sheet, in further alternative embodiments may have the donning agent associated with zones or regions within a sheet side, or layer side. For example, such zones or regions may be parallel rows of donning agent on the substrate. Such an embodiment would allow for higher absorbency in those zones or regions, which did not include the donning agents.

In one embodiment, the cellulosic material substrate is a nonwoven-reinforced cellulosic material, meaning that it includes a nonwoven material within its structure to assist in either strength attributes or elastic attributes. Such material is desirably a scrim reinforced material such as that available from the Kimberly-Clark Corporation under the designation Absorbent Towel 4110SRM. Desirably, a towel of the present invention has a basis weight of between about 15 to 110 grams per square meter, more desirably between about 25 and about 80 gsm, still more desirably between about 60 and 80 grams per square meter (gsm), and still even more desirably about 70 gsm.

An exemplary scrim reinforced material as described in U.S. Pat. No. 4,001,472 to Thomas et al, which is incorporated by reference herein in its entirety. In order to create a hand towel with acceptable bulk and absorbency, it is generally desirable to use high basis weight amounts of cellulosic material and/or to subject the product to bulking techniques such as creping or embossing, as shown in U.S. Pat. No. 3,025,199, which is incorporated by reference in its entirety. As shown in FIG. 1, such a nonwoven scrim-reinforced cellulosic material 10, is formed by any known method and apparatus, such as that described in U.S. Pat. No. 2,842,202 to H. W. Hirschy, incorporated by reference in its entirety. The scrim material may be formed of either extruded polymeric materials or preformed polymeric materials. The warp end fill threads of the scrim 12 can be adhesively bonded together to form the scrim by any conventional means. The scrim employed can have from 1 to 12 or more threads per inch in each direction. Any conventionally employed strand/filamentous material, such as the synthetic polymers nylon, rayon, polyester, polyolefins such as polyethylene and polypropylene, and block copolymers, such as the KRATON® block copolymer series of polymers, can be employed for the scrim material. The denier can range for example, from about 20 to about 150. The cellulosic wadding 14 attached to the scrim, can be any of the conventionally known types and can comprise one or more plies. When more than two plies are utilized (either one on each side of the scrim, or multiple layers on top of each other), the individual plies are desirably independently inter-bonded by adhesive applied to a sufficient area of adjacent surfaces of the multiple plies to hold the plies together. As will be apparent to those skilled in the art, the adhesive will normally be applied in a discontinuous pattern so that the desired interbonding is achieved with a minimum of adhesive and without decreasing the flexibility of the multi-ply layer. The drier basis weight per ply may be in one embodiment between about 4 and 13 lbs/2880 sq/ft. The cellulosic wadding can in one embodiment contain the ability to stretch from its original length, in the 10 to 150% ranges.

Such a scrim-based substrate is manufactured in accordance with the process described in U.S. Pat. No. 4,001,472, incorporated by reference herein in its entirety. The nonwoven reinforced substrate may additionally include topographical variations, such as embossing patterns, or ridges and valleys, for further bulkiness.

The nonwoven reinforced cellulosic material includes a chemical treatment of a donning agent that is easily transferable to the hands of a user during a drying operation. Such donning agent is desirably a lubricant such as a water soluble material that will easily transfer to the hands of a user upon contact with water during hand drying, but that will not significantly interfere with the drying operation. The chemical treatment is desirably applied to the nonwoven-reinforced cellulosic material following production of the web material. Such chemical treatment is therefore applied in a post-processing step. The lubricant may be applied as a spray or by other known web treatment method, and subsequently allowed to dry. Such drying is accomplished under either ambient conditions or via a heating step so that the donning agent is in a dried condition prior to use. Whether to utilize nonambient conditions to dry the web will be determined by the amount of treatment applied to the web. The chemical treatment may either be applied such that it impregnates the interstitial spaced of the cellulosic web, or as a surface treatment or coating only. In either case, the chemical treatment associates with the web. For instance, the treatment can be applied by spray methods, dip and squeeze methods printing, or other traditional web treatment application methods, although spray and print methods are desirable.

An example of a lubricant (donning agent) that can be utilized with the invention includes a water soluble donning agent which can be selected from the wetting agent group of waxes, cationic polymers, surfactants, materials which act like either waxes, cationic polymers, surfactants, or silicones, or combinations thereof. For example, a behen-trimonium methodsulfate and sterearyl alcohol (Incroquat Behynl TMS, From Croda Inc.) can be used for such a purpose. Such waxes can be self emulsifying waxes, such as mixtures of cetearyl alcohol and cetearyth-20 (Cosmowax from Croda), stearyl alcohol and cetereath 20 (Croda Cosmo wax K), glyceryl sterate SE (Lexemul 530), mixtures of cetearyl alcohol and PEG-40 castor oil and stearylalkonium chloride (Croda Incroquat CR concentrate), glyceryl laurate SE, glyceryl oleate SE, PEG-2 sterate, PEG-2 oleate, PEG-2 laurate, and combinations thereof.

Other compositions that act like self emulsifying waxes include mixtures of fatty acids or fatty esters, nonionic surfactants, anionic surfactants, and cationic surfactants that have at least 20 carbon atoms. Such materials would include straight and branched chain fatty acids, saturated and unsaturated alcohols.

Suitable cationic polymers include cellulose, collagen, and vinylpyrolidone derived cationic polymers, and combinations thereof. Such are exemplified by Ucare Polymer JR400 (from Amerchol) and Celquat SC 240 (National Starch). Another cationic material includes a quaternary ammonium compound, such as Verisoft BTMS (available from Goldschmidt Chemical Corp. of Dublin, Ohio).

As has been previously stated, silicones may also be used. Such include nonreactive or mixtures of reactive and nonreactive silicones. Desirably, the silicone is a liquid silicone. Examples include polysiloxanes such as polydimethylsiloxane and analogous compounds in which the methyl residues are replaced by other functions such as the alkyl, aryl, aralkyl, alkenyl, alkoxy, and the like. Other specific examples include aminosilicones, polyether-modified amino silicones, dimethicone, quaternary silicone, silicone polyethers, polyether epoxy silicones, and silanol fluids. Other examples include DC-365 (Dow Corning).

The donning agent desirably includes between about 0.1% to 4% by weight wetting agent, and between about 0.1% to about 4% by weight silicone in water. It is desirable to transfer an effective amount of donning agent to each hand from the towel, to allow for ease of donnability. For instance a coating weight of between about 0.01 to 0.2 g/glove would be effective for donnability of the glove. In one embodiment, it is desirable that between about 0.1 gsm and 20 gsm be added to the towel to provide an effective amount of donning agents for between two to four gloves. It should be recognized that the addition of larger amounts of certain donning agents, such as silicones will decrease the ability of the towel to absorb moisture. Therefore, it is desirable in one embodiment, for one surface (or layer of a multi-layered embodiment) of the substrate to be free of donning agents, in order to ensure adequate absorption of moisture, while continuing to provide donning agent delivery.

In one embodiment, it is desirable that a donning agent amount of about 2 gsm be added to the towel following towel manufacture. Such may be added for example, by spraying a 2% solution (of the materials previously described) to the towel so as to impregnate the towel (2 wt % in water) or in the alternative to topically treat the towel. For example, treatment compositions may be applied at levels of above 1 percent to as much as 30 weight percent, based on the weight of the substrate. The towel could then be dried at between about 210° F. to 350° F. It should be noted that such drying conditions will vary depending on the amount of donning agent applied and the substrate employed. For instance, if the substrate includes a nonwoven material, the drying temperature will necessarily be less than the melting temperature of the nonwoven. Such drying may be accomplished by any known web heating means, such as drying hoods and can dryers for example. In certain circumstances, drying may be unnecessary, as such a small amount of liquid is added to the previously dried towel. For instance, in a further alternative, between about 0.1 and 0.5% of a solution is sprayed onto the towel. Percent in this instance is by weight of the towel.

Figure 2:
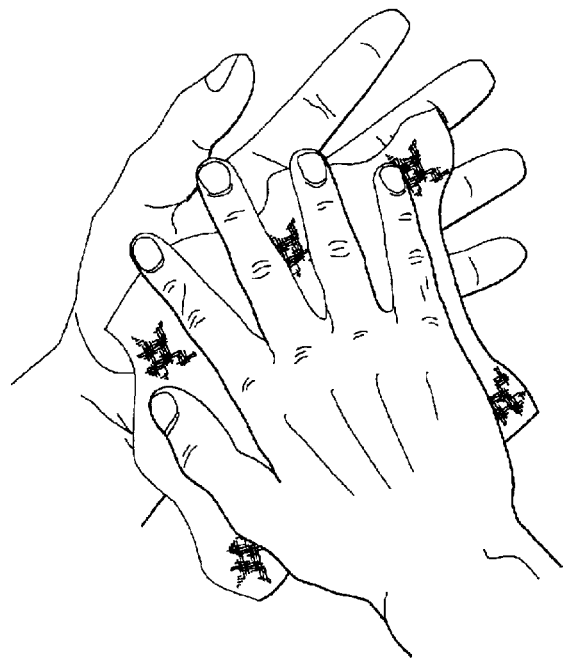
FIG. 2 is a partial perspective view of a hand drying operation utilizing a towel of the present invention.

In a hand drying operation utilizing the towel/delivery system, a medical practitioner would wash/scrub as he/she normally would, and then dry his/her hands using the towel as shown in FIG. 2, which illustrates a perspective view of a hand drying operation using the towel of the present invention. In the operation, the substrate is contacted with the hands of the medical practitioner, following washing. In a simultaneous action, the towel dries the hands and a donning gent is transferred from the towel/substrate to the user's hands. Upon conclusion of the hand drying operation, the medical practitioner can then discard the hand towel as he/she would other such medical waste. The medical practitioner would then proceed to don his/her elastomeric gloves using acceptable glove donning procedures.

In an alternative embodiment, the cellulosic material can be a hydroentangled material, such as that available from Kimberly-Clark under the designation Huck Towel, of a hydroentangled construction of approximately 104 gsm. Such a towel may be manufactured using a spunbond and cellulosic material hydroentangling process. Hydroentangled materials are described in U.S. Pat. No. 5,284,703 which is incorporated by reference herein in its entirety. Such a process allows for the production of a high pulp content nonwoven composite fabrics. As with the previous example, such a substrate would be exposed to chemical treatment following production, by either spray application, printing, dipping, or other type of post-manufacturing web treatment application.

In still a further alternative embodiment, a web fashioned from a stretch bonded laminate material may be employed as a towel substrate. Such a nonwoven substrate may include either nonwoven layers which have been treated to be hydrophilic and absorbent, or inherently hydrophilic and absorbent layers (i.e. layers which include cellulosic materials). Again, as in the previous embodiments, such substrates would then be treated with a donning agent, and if necessary dried, following web production.

In still a further alternative embodiment, it should be recognized that the towel can be manufactured by known towel manufacturing processes (without a nonwoven component), such as in known wet laid processes, and then dried. Such towels, for instance include wet strength reinforced towels, as are known in the art. Such a towel would subsequently be treated with a donning agent as previously described, and dried if necessary.

Another suitable material for practicing the present invention is a non-woven composite material commonly referred to as "coform." Coform as has been previously discussed, is an air-formed matrix material of thermoplastic polymeric meltblown fibers such as, for example, microfibers having an average fiber diameter of less than about 10 microns, and a multiplicity of individualized absorbent fibers such as, for example, wood pulp fibers disposed throughout the matrix of polymer microfibers and engaging at least some of the microfibers to space the microfibers apart from each other. The absorbent fibers are interconnected by and held captive within the matrix of microfibers by mechanical entanglement of the microfibers with the absorbent fibers, the mechanical entanglement and interconnection of the microfibers and absorbent fibers alone forming a coherent integrated fibrous structure.

The coherent integrated fibrous structure can be formed by the microfibers and absorbent fibers without any adhesive, molecular or hydrogen bonds between the two different types of fibers. The absorbent fibers are preferably distributed uniformly throughout the matrix of microfibers to provide a homogeneous material. The material is formed by initially forming a primary air stream containing the melt blown microfibers, forming a secondary air stream containing the wood pulp fibers, merging the primary and secondary streams under turbulent conditions to form an integrated air stream containing a thorough mixture of the microfibers and wood pulp fibers, and then directing the integrated air stream onto a forming surface to air form the fabric-like material. The microfibers are in a soft nascent condition at an elevated temperature when they are turbulently mixed with the wood pulp fibers in air.

It should therefore be understood that the present invention is suitable for use with a wide range of sheet materials. By way of example only, additional sheet and sheet-like materials believed suitable for use with the present invention are described in the following U.S. Pat. Nos. 3,650,882, 4,001,472; 4,100,324; 4,833,003; 5,048,589; 5,399,412; 5,776,306; 6,077,590; 6,273,996; and so forth, each incorporated by reference herein in their entirety.

Still, in a further alternative embodiment, cloth substrates, as opposed to paper-based materials, may be utilized as the basis of the towel substrate. Such cloth substrates include absorbent/hydrophilic cellulosic based cloths and other cloth materials which have been treated to be hydrophilic/absorbent. Cloth substrates are somewhat less desirable, however, as a result of the difficulty in disposing of such waste after use, and the difficulties associated with laundering such materials, as well as linting problems.

Still in a further embodiment, nonwoven webs may be used as the basis of the towel substrate. However, since nonwoven webs are generally made from hydrophobic polymeric materials, such as polyethylene and polypropylene polymers, such materials should be treated to be hydrophilic and absorbent, prior to being made into hand towel sheets. Such materials can be made hydrophilic by application/treatment of nonionic surfactants for example or may be multilayered and further, may include superabsorbent materials.

It should be recognized that it is desirable that in each of the above described embodiments, the donning agent be biocompatible and sterilizable, (and the substrate be sterilizable) such that should it come in contact with an open wound, possibilities of infection or allergic reaction are reduced or eliminated.

In an alternative embodiment of each of the above substrates, the substrate further includes an antimicrobial agent/virucidal treatment that is capable of being transferred to the hands of a user. The antimicrobial/virucidal agent is desirably biocompatible as well, and desirably, some residual antimicrobial/virucidal agent remains on the towel following use. The application of antimicrobial agents to absorbent substrates is described in U.S. Pat. Nos. 4,828, 912, 5,569,732, and EPO 869 216 A1, which are incorporated herein by reference in its entirety.

In a further alternative embodiment of the above substrates, the substrate further includes a skin health agent. In particular, the substrate may include aloe vera, such as aloe vera concentrate, vitamin E, or other emollient/moisturizer that may be transferred along with the donning agent to the hands of the towel's user. Application of such a skin health agent is described in WO 01/47699 A1 and U.S. Pat. Nos. 4,481,243, 4,513,051, and 5,665,426 (for reducing skin irritation) which are incorporated herein by reference in its entirety.

In still a further alternative embodiment of the above substrates, the substrate may further include an antimicrobial agent within the towel, that is not transferable, but that has been placed in the towel to assist in maintaining a sterile environment in the towel itself. Each of the above substrate materials is desirably capable of being sterilizable prior to being used in their capacity as a hand towel.

In still a further embodiment, an alternative method of utilizing such donning agent delivery system includes use of such towel to deliver a donning layer to the exposed surface of a glove, as opposed to the skin on a medical practitioner's hand. In many cases during surgery or other medical procedure, doctors and nurses prefer to have two pairs of gloves worn on their hands at one time. This practice is known as "double gloving". This practice is utilized in order to enhance the protection of the glove wearer from sharp objects and single layer glove failure. Donning the second glove can be as difficult as the first glove.

To aid in this process, the glove wearer may utilize a towel as previously described, to prepare the first gloves outer surface and thus make donning the second pair easier. By doing so, the first glove's outer surface will also be free of blood and other fluids that are prevented from being trapped between the glove layers. If antimicrobial/virucidal treatments are used in the towel, this could also provide benefits in killing any live organisms that may exist on the first glove outer surface. Therefore, a method is now available for donning a second pair of elastomeric gloves, which involves washing the hands, and contacting the hands with a substrate that both simultaneously dries the hands and transfers a donning agent to the hands. This step is followed by contacting the outer glove surfaces of the gloves that are on the hands with the towel in order to impart additional donning agent to the outer surface of the worn gloves, and then donning a second pair of gloves over the first pair already on the hands.

While the invention has been described in detail with respect to the specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. An absorbent substrate, comprising a flexible substantially planar sheet of at least one layer, having a front side and a back side, with a donning agent associated with at least one side of said sheet, wherein said donning agent is transferable from said sheet.

2. The substrate of claim 1 wherein the said donning agent is a bio-compatible and sterilizable substance.

3. The substrate of claim 2 wherein the said sheet is selected from a cellulosic-based material, a stretch bonded laminate material, a nonwoven reinforced cellulosic-based material; a nonwoven material, a cloth material or a combination thereof.

4. The substrate of claim 1 wherein said donning agent is selected from a wetting agent, a substance that acts as a wetting agent, a silicone, and combinations thereof.

5. The substrate of claim 1, further comprising at least one substance, on or within at least one side of said sheet, selected from the group consisting of skin health agents, residual antimicrobial substrate agents, antimicrobial agents or combinations thereof.

6. The substrate of claim 5 wherein said skin health agents are selected from the group consisting of aloe vera, vitamin E, emollients and combinations thereof.

7. The substrate of claim 1 wherein said substrate in a nonwoven reinforced cellulosic-based substrate and said nonwoven material is scrim.

8. An absorbent substrate, comprising a flexible substantially planar sheet of at least one layer, having a front side and a back side, with a donning agent, skin health agent and antimicrobial agent associated with at least one side of said sheet, wherein said donning agent, skin health agent and antimicrobial agent are each transferable from said sheet.

9. The absorbent substrate of claim 8, wherein said donning agent is associated with both sides of said sheet.

10. The absorbent substrate of claim 8, wherein said absorbent substrate includes multiple layers.

11. An absorbent substrate, comprising a flexible substantially planar sheet of at least one layer, having a front side and a back side, where said sheet has at least one distinct absorbent region and at least one distinct donning agent region with a donning agent associated with said donning agent region, wherein said donning agent is transferable from said sheet.

12. The substrate of claim 11 wherein the front side of said sheet comprises said donning agent region.

13. The substrate of claim 11 wherein the donning agent region is comprised of parallel rows of donning agent on the substrate separated by parallel rows of absorbent regions.

14. The substrate of claim 11 wherein the said donning agent is a bio-compatible and sterilizable substance.

15. The substrate of claim 13 wherein the said sheet is selected from a cellulosic-based material, a stretch bonded laminate material, a nonwoven reinforced cellulosic-based material; a nonwoven material, a cloth material or a combination thereof.

16. The substrate of claim 11 wherein said donning agent is selected from a wetting agent, a substance that acts as a wetting agent, a silicone, and combinations thereof.

17. The substrate of claim 11, further comprising at least one substance, on or within at least one side of said sheet, selected from the group consisting of skin health agents, residual antimicrobial substrate agents, antimicrobial agents or combinations thereof.

18. The substrate of claim 17 wherein said skin health agents are selected from the group consisting of aloe vera, vitamin E, emollients and combinations thereof.

19. The substrate of claim 11 wherein said substrate in a nonwoven reinforced cellulosic-based substrate and said nonwoven material is scrim.

* * * * *